United States Patent [19]

Anderson

[11] 4,180,078
[45] Dec. 25, 1979

[54] LEAD CONNECTOR FOR A BODY IMPLANTABLE STIMULATOR

[75] Inventor: Kenneth M. Anderson, Bloomington, Minn.

[73] Assignee: Medtronic, Inc., Minneapolis, Minn.

[21] Appl. No.: 894,360

[22] Filed: Apr. 7, 1978

[51] Int. Cl.² ............................................. A61N 1/36
[52] U.S. Cl. ............................................. 128/419 PG
[58] Field of Search ........... 128/419 C, 419 E, 419 P, 128/419 PG, 419 PS, 419 R, 42, 422, 423

[56] References Cited

U.S. PATENT DOCUMENTS

| | | | |
|---|---|---|---|
| 3,822,707 | 7/1974 | Adducci et al. | 128/419 P |
| 3,908,668 | 9/1975 | Bolduc | 128/419 P |
| 3,938,507 | 2/1976 | Sarnoff et al. | 128/2.06 F |

Primary Examiner—William E. Kamm
Attorney, Agent, or Firm—Lindquist & Vennum

[57] ABSTRACT

An improved connector for interconnecting a furcated lead and signal generator to form a body implantable stimulator. The connector is secured to the signal generator to form a signal generator assembly. Jacks are provided in the connector to receive the lead furculae while facilitating conformance of furculae to the configuration of the signal generator assembly on wrapping of the furculae around the signal generator assembly. In a preferred embodiment, the jacks accept the furculae at different distances from the signal generator to allow a thinner signal generator assembly and at different depths to compensate for the difference in distance of the jacks from the signal generator.

16 Claims, 5 Drawing Figures

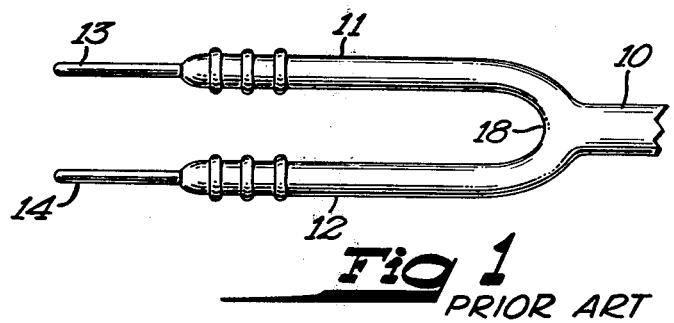
Fig 1 PRIOR ART
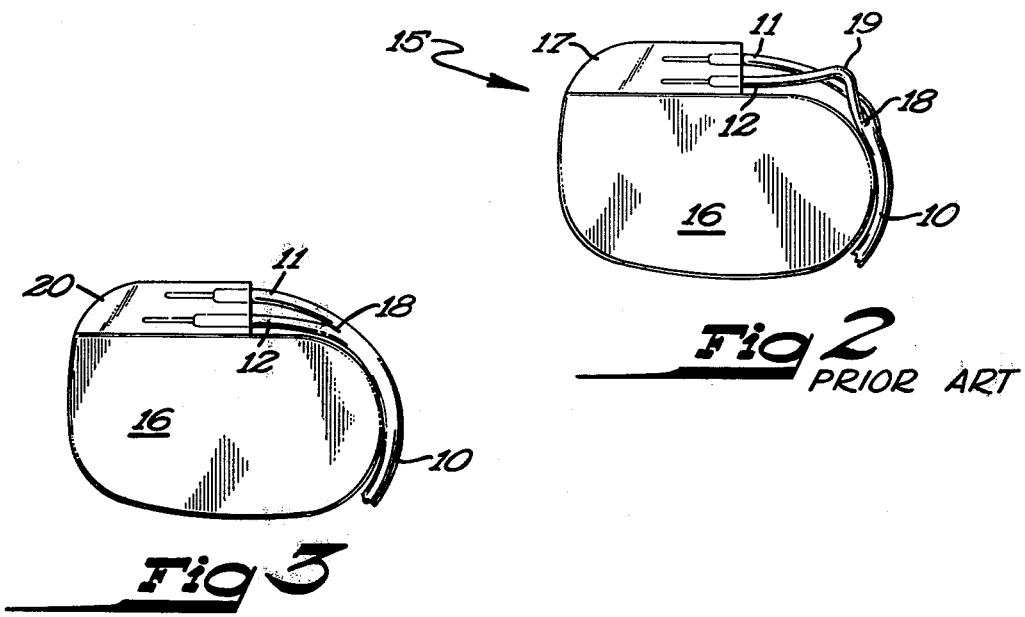
Fig 2 PRIOR ART
Fig 3
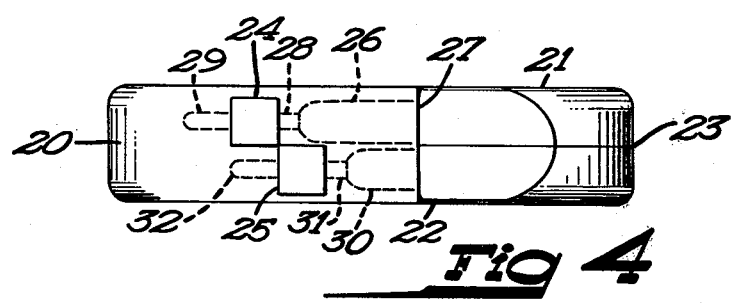
Fig 4
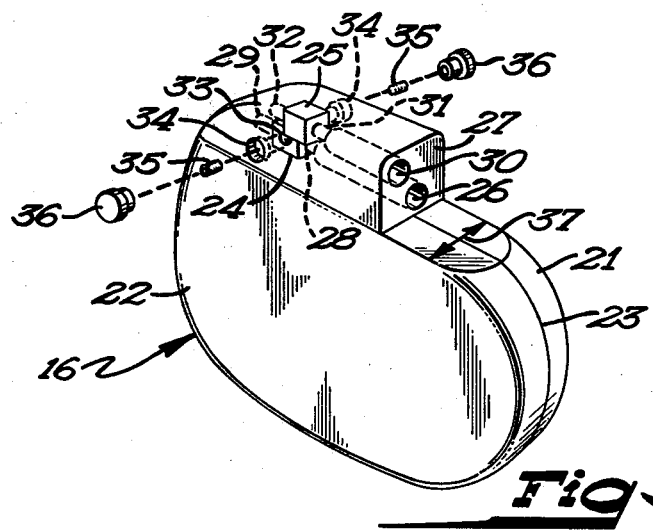
Fig 5

LEAD CONNECTOR FOR A BODY IMPLANTABLE STIMULATOR

BACKGROUND OF THE INVENTION

Body implantable stimulators are known to the prior art, the most common being the well-known cardiac pacemaker. Within such stimulators, advances in power source and electronic technology have significantly reduced in the volume required by the signal generating components while providing increases in power source life and an enhanced adaptability of the operating characteristics.

While the reduction in volume of the signal generating components affords a tremendous opportunity to reduce the size of the stimulator itself, that opportunity is restricted by the prior art interconnection between the signal generator and the lead. For example, in the typical prior art bipolar body stimulator it has been a common practice to employ a bifurcated lead with the lead furculae being inserted in side-by-side relation within a connector assembly. However, the available volume reduction of the signal generator allows a reduction in thickness to a dimension which is unable to accommodate the prior art lead furculae in side-by-side relation. Therefore, to take advantage of the potential for reduced signal generator thickness it has been suggested that the lead connector accept the furculae at different distances from the signal generator in a "over-/under" relationship. That is, it has been suggested that the connector accept one furcula at a position relatively adjacent the signal generator and the second furcula at a position more distant from the signal generator such that the thickness requirement of the lead connector can be compatible with the potential reduced thicknesss of the signal generator. Alternatively, it has been suggested that the diameter of at least the lead furculae be reduced such that the prior art side-by-side arrangement may be continued. However, inasmuch as the stress within a lead varies geometrically in accordance with its dimensions (radius, for example) a significant reduction in size necessarily results in an even more significant, and perhaps prohibitive, increase in stress concentration in the lead. In addition, alteration in the size of lead from prior art standards will result in the necessity of replacement of a lead on replacement of a signal generator assembly or in the use of adapters, neither concept having a high degree of acceptability. Accordingly, the use of a "over/under" arrangement appears to have the greatest potential for acceptance.

Typical prior art bifurcated leads have furculae of equal length. In addition, prior art lead systems are made to standardized lengths often resulting in the use of a lead of greater length than is necessary in a particular implant. The excess length is typically taken up by wrapping the excess lead and furculae around the signal generator assembly prior to placement of the signal generator assembly in the "pocket". In view of the equal furcula lengths of existing lead assemblies, this "wrapping" has led to difficulties in the conversion from a "side-by-side" to a "over/under" connector arrangement. That is, a mere reconfiguration of a connector from a "side-by-side" to a "over/under" relationship results in an excess furcula length in the furcula closest to the signal generator, the excess length interfering with a proper wrapping of the upper furcula around the signal generator assembly. In addition, the excess length of the furcula closest to the signal generator produces pockets which encourage fibrosis. Thus, while a "over/under" arrangement allows the use of existing leads systems with a signal generator of reduced thickness, wrapping and fibrosis problems result from that arrangement.

SUMMARY OF THE PRESENT INVENTION

The present invention provides an "over/under" connector assembly for interconnecting a furcated lead and signal generator to form a body implantable stimulator. Thus, the present invention allows the use of existing lead systems with signal generators of reduced thickness. In addition, the present invention allows the "over/under" arrangement of the furculae within the connector assembly while facilitating the conformance of the furculae to the configuration of the signal generator assembly on wrapping of the furculae around the generator assembly, the interference of the furculae with each othe being eliminated and the fibrosis problem greatly reduced. In a preferred embodiment, the connector accepts the lead furculae at depths which compensate for different distances between the furculae and the signal generator. That is, the furculae received by the connector at a position closer to the signal generator are received to a greater depth than the furculae received at a greater distance from the signal generator thereby accommodating those differences in spacing of the furculae from the signal generator.

BRIEF DESCRIPTION OF THE DRAWINGS

FIG. 1 illustrates the proximal end of a typical prior art bifurucated lead system.

FIG. 2 illustrates the interference between furcula of a prior art "over/under" furcula arrangement.

FIG. 3 illustrates the concept of the present invention.

FIG. 4 the top view of a signal generator assembly illustrating the present invention.

FIG. 5 the perspective view of a signal generator assembly illustrating the present invention.

DETAILED DESCRIPTION OF THE DRAWINGS

FIG. 1 shows a typical prior art bifurcated lead having a main lead body 10 and furculae 11 and 12 joining at a junction 18. The furculae 11 and 12 terminate in pin contacts 13 and 14, respectively, in known manner. The pin contacts are electrically connected to electrical conductors contained within the furculae 11 and 12 and body 10 which extend between the pin contacts 13 and 14 and electrodes carried by the body 10, in known manner. The electrodes may consist of two active electrodes in a bipolar system or a single active electrode and a indifferent electrode in a unipolar system, also in known manner. Typically, the furculae 11 and 12, including the pins 13 and 14, are of equal length.

Referring now FIG. 2, there is shown a signal generator assembly designated generally at 15 including a signal generator 16 and connector assembly 17. Signal generator 16 includes all the necessary signal generating components, including a power source or sources, all of which are known to the prior art. The connector 17 is adapted to mechanically and electrically interconnect the pin contacts 13 and 14 to the signal generating components of signal generator 16, the particular form of mechanical and electrical interconnection forming no part of the present invention. That is, it is known to insert pin-type contacts within a connector assembly such as that illustrated at 17 to electrically and mechanically interconnect those contacts with the signal generating components and any known interconnection system may be employed in conjunction with the present invention.

As illustrated in FIG. 2, the prior art connector 17 is merely a reorientation of the "side-by-side" configuration of the prior art. That is, instead of the connector assembly receiving the pin contacts 13 and 14 (and portions of the furculae 11 and 12) in a "side-by-side" relationship, the connector assembly 17 accepts those contacts and furculae in a "over/under" relationship. As discussed above, this may be necessary or desirable to render a prior art lead system compatible with a thinner signal generator assembly. As illustrated in FIG. 2, pin contacts 13 and 14 are inserted to the same insertion depth within the connector 17, as was the common practice with the "side-by-side" configuration of prior art connectors. However, in view of different distances of the furculae from the signal generator 16, and the fact that the furculae 11 and 12 and lead body 10 are typically wrapped around the signal generator assembly formed by signal generator 16 and connector 17, there is a different distance between the exit of furcula 11 from connector 17 and furcula junction 18 and the exit of furcula 12 from connector 17 and the junction 18. Thus, as furcula 11 is wrapped to conform to the configuration of the signal generator assembly, furcula 12, being of the same length as furcula 11, has the same length to span a shorter distance. This results in upward protrusion of furcula 12 as illustrated at 19. The protrusion 19 interfers with the wrapping of furcula 11 around the signal generator assembly and also results in an interstice between it and the signal generator 16 to encourage fibrosis.

The concept of the present invention is illustrated in FIG. 3 wherein the lead system of FIG. 1 and the signal generator 16 of FIG. 2 are employed. However, the connector assembly 20 of FIG. 3 is adapted to accept the furculae 11 and 12 at different depths to accommodate the different distances between the furculae and the signal generator 16. That is, the furcula 12 is accepted to a greater insertion depth within the connector 20 than is the furcula 11, thereby taking up that length of furcula 12 which forms the protrusion 19 illustrated in FIG. 2. This not only enhances the wrapping of the furculae when an "over/under" relationship is employed within the connector 20 but also reduces fibrosis. In essence, as illustrated in FIG. 3, the connector 20 accepts the furculae 11 and 12 at depths established in accordance with the distance between them and the signal generator 16 to facilitate the conformance of the furculae to the configuration of the signal generator assembly on wrapping of the furculae around the signal generator assembly. The closer a furcula to the signal generator 16, the greater the depth to which it will be accepted within the connector 20.

Referring now to FIG. 4 there is shown a signal generator assembly including a connector 20 and signal generator 16. Signal generator 16 is typically formed as two body halves 21 and 22 which are welded together at a seam 23, in known manner, the signal generating components being housed within the signal generator body halves 21 and 22. The connector 20 may be formed on the signal generator 16 by an epoxy molding process, in known manner, or may be formed as a premolded member mechanically or adhesively secured to the signal generator 16. The connector 20 contains two terminals 24 and 25 each of which are positioned along separate jacks within the connector 20 with terminal 24 being positioned a greater distance from face 27 of connector 20 then terminal 25. The jack associated with terminal 24 includes a first portion 26 extending from face 27 of connector 20, second portion 28 extending between the portion 26 and the terminal 24 and a portion 29 extending from terminal 24. Similarly, the second jack includes a portion 30 extending from face 27, a second portion 31 extending between portion 30 and terminal 25 and a portion 32 extending from terminal 25. Jack portions 26 and 30 are adapted to receive the furculae 11 and 12, respectively, with pin 13 being guided by the jack portions through portion 28, terminal 24 and into portion 29 while pin 14 is guided through portion 31, terminal 25 and into portion 32. Electrical and mechanical communication between the terminals 24 and 25 and pin contacts 13 and 14, as well as electrical communication between those terminals 24 and 25 and the components housed within signal generator 16 may be made in any convenient and known manner without departing from the scope of present invention. For the purpose of the present invention, it is sufficient that portions 30, 31 and 32 be positioned at a greater distance from signal generator 16 than the respective portions 26, 28, and 29 in a "over/under" arrangement with portion 26 having a greater length than portion 30 so as to accept a greater amount of furcula 12 than the amount of furcula 11 which is accepted by portion 30, the difference in length between portions 26 and 30 being dependent on the difference in distance between them and signal generator 16. Also, it is not necessary for the purposes of the present invention that the jacks be centered with respect to the signal generator 16. In the embodiment illustrated in FIG. 4, the signal generator 16 is symmetrical with respect to the seam 23, seam 23 forming the center line of signal generator 16, and both jacks are off-set from the centerline. Within the scope of the present invention, one or both of the jacks may be off-set from the center line of the signal generator 16 such that those jacks have a skewed relation within the connector 20.

Referring now to FIG. 5, there is shown a perspective view of a preferred embodiment of the present invention, specifically, the embodiment illustrated in FIG. 4 in greater detail. Two jacks extend from face 27 to terminals 24 and 25. As illustrated in FIG. 5, the terminals 24 and 25 are provided with threaded bores 33 (one shown) which are accessible from outside connector 20 via apertures 34 such that set screws 35 may be engaged within the threads of bores 33 to maintain the pin contacts 13 and 14 within the terminals 25 and 24, respectively, the apertures 34 being sealed by grommets 36, all in known manner. Again, as illustrated in FIG. 5, the jacks have an "over/under" relationship so as to accommodate a greater reduction in thickness (the dimension illustrated by arrow 37 in FIG. 5) than would be possible with a "side-by-side" relation. Also, the jack closer to the signal generator 16 receives a greater length of furcula than the more distant jack. In the preferred embodiment illustrated in FIG. 5, the jacks are in skewed relation within the connector 20 meaning that a line connecting them is oblique with respect to a plane through the center line of signal generator 16.

Of course many modifications and variations of the present invention are possible in light of the above teachings. For example, the present invention is presented in the context of accommodating different distances between the jacks and the signal generator. For the purposes of this specification and claims, a jack is more distant from the signal generator than another jack if its position in the connector is more outward than that of the other jack. Also, two jacks are illustrated for accepting the furculae of a bifurcated lead. Obviously, the concepts of the present invention may be extended to furcated leads having more than two furculae. In addition, the present invention may also be employed to accommodate different furculae lengths in furcated leads, different furculae insertion depths being employed to facilitate the conformance of the furculae to the configuration of the signal generator assembly on wrapping of the furculae around the signal generator assembly. It is therefore to be understood that, within the scope of the appended claims, the invention may be practiced otherwise than as specifically described.

What is claimed is:

1. In a body implantable stimulator of the type having furcated lead means and a signal generator assembly including signal generator means and connector means for interconnecting said signal generator means and the lead means furculae, at least the lead means furculae being wrapped around said signal generator assembly on implantation, the improvement wherein said connector means comprises jack means for receiving said lead means furculae, said jack means comprising means for compensating for non-uniform spacing of said jack means from said signal generator means to facilitate the conformance of said furculae to the configuration of said signal generator assembly on wrapping of said furculae around said signal generator assembly.

2. The stimulator of claim 1 wherein said facilitating means comprises means for compensating for different furculae lengths.

3. In a body implantable stimulator of the type having signal generator means, furcated lead means and connector means interconnecting said signal generator means and the lead means furculae, the improvement wherein said connector means comprises at least two jack means located within said connector means for receiving said lead means furculae, at least one of said jack means being more distant from said signal generator means than others of said jack means, said jack means comprising means for accommodating the different distances of said jack means from said signal generator means.

4. The stimulator of claim 3 wherein said accommodating means comprises means for receiving said furculae at depths established in accordance with the distance between a jack means and the signal generator means.

5. The stimulator of claim 4 wherein a jack means having a greater distance from said signal generator means has a lesser furcula receiving depth.

6. The stimulation of claim 4 wherein said compensating means comprises means for receiving said furculae at depths established in accordance with the distance between a jack means and the signal generator means.

7. The stimulator of claim 6 wherein a jack means having a greater distance from said signal generator means has a lesser furcula receiving depth.

8. In a body implantable stimulator of the type having furcated lead means and a signal generator assembly including signal generator means and connector means for interconnecting said signal generator means and the lead means furculae, at least the lead means furcula being wrapped around said signal generator assembly on implantation, the improvement wherein said connector means comprises at least two jack means for receiving said lead means furculae, at least one of said jack means being more distant from said signal generator means than others of said jack means, and said jack means comprising means for compensating for the different distances of said jack means from said signal generator means to facilitate the conformance of said furculae to the configuration of said signal generator assembly on wrapping of said furcula around said signal generator assembly.

9. In a body implantable stimulator of the type having signal generator means, bifurcated lead means and connector means interconnecting said signal generator means and the lead means furculae, the improvement wherein said connector means comprises two jack means spaced from each other and said signal generator means within said connector means for receiving said furcula, said jack means comprising means for accommodating a difference in spacing of said jack means from said signal generator means.

10. The stimulation of claim 9 wherein said accommodating means comprises means for receiving said furculae at depths established in accordance with the distance between a jack means and the signal generator means.

11. The stimulator of claim 10 wherein a jack means having a greater distance from said signal generator means has a lesser furcula receiving depth.

12. The stimulator of claim 11 wherein said jack means are in skewed relation within said connector means.

13. The stimulator of claim 9 wherein said lead means furcula terminate at pin contacts, said connector means comprising terminal means within said connector means and said jack means comprising means for accepting said lead means furculae to guide said pin contacts into contact with said terminal means.

14. The stimulator of claim 13 wherein said accommodating means comprises means for maintaining said terminal means at different depths within connector means.

15. The stimulator of claim 13 wherein said accommodating means comprises means for accepting different lengths of said lead means furculae.

16. The stimulator of claim 9 wherein said accommodating means comprises means for receiving different lengths of said lead means furculae.

* * * * *